(12) United States Patent
Swierkowski

(10) Patent No.: US 6,558,523 B1
(45) Date of Patent: May 6, 2003

(54) INJECTOR-CONCENTRATOR ELECTRODES FOR MICROCHANNEL ELECTROPHORESIS

(75) Inventor: Stefan P. Swierkowski, Livermore, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/545,616

(22) Filed: Apr. 10, 2000

(51) Int. Cl.$^7$ .............................................. G01N 27/453
(52) U.S. Cl. ........................................................ 204/604
(58) Field of Search ........................................ 204/604

(56) References Cited

U.S. PATENT DOCUMENTS

| | | | |
|---|---|---|---|
| 5,877,580 A | * 3/1999 | Swierkowski | 310/328 |
| 6,110,332 A | * 8/2000 | Swierkowski | 204/242 |
| 6,110,339 A | * 8/2000 | Yager et al. | 204/451 |
| 6,171,378 B1 | * 1/2001 | Manginell et al. | 55/DIG. 5 |
| 6,176,990 B1 | * 1/2001 | Yager et al. | 204/601 |
| 6,193,866 B1 | * 2/2001 | Bader et al. | 204/450 |
| 6,236,945 B1 | * 5/2001 | Simpson et al. | 435/6 |
| 6,261,430 B1 | * 7/2001 | Yager et al. | 204/450 |
| 6,387,234 B1 | * 5/2002 | Yeung et al. | 204/451 |

* cited by examiner

*Primary Examiner*—Jill Warden
*Assistant Examiner*—Jennine M Brown
(74) *Attorney, Agent, or Firm*—L. E. Carnahan; Alan H. Thompson

(57) ABSTRACT

An input port geometry, with injector-concentrator electrodes, for planar microchannel array for electrophoresis. This input port geometry enables efficient extraction and injection of the DNA sample from a single input port. The geometry, which utilizes injector-concentrator electrodes, allows simultaneous concentration, in different channels, of the sample into a longitudinally narrow strip just before releasing it for a run with enhanced injection spatial resolution, and time resolution. Optional multiple electrodes, at a different bias than the concentrator electrodes, may be used to discriminate against sample impurity ions. Electrode passivation can be utilized to prevent electrolysis. An additional electrode in or on the input hole can better define the initial loading. The injector-concentrator electrodes are positioned so that they cross the drift channel in a narrow strip at the bond plane between the top and bottom plates of the instrument and are located close to the inlet hole. The optional sample purification electrodes are located at a greater distance from the input hole than the injector-concentrate electrodes.

15 Claims, 2 Drawing Sheets

INJECTOR-CONCENTRATOR ELECTRODES FOR MICROCHANNEL ELECTROPHORESIS

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to microchannel electrophoresis instruments, particularly to input sample insertion geometry of the microchannels, and more particularly to the input port geometry for planar microchannel arrays which include at least injector-concentrator electrodes that enable efficient extraction and injection of a sample from the input port.

Current emerging alternative methods to commercial slab-gel electrophoresis (e.g. for DNA sequencing) are systems based on discrete drift channels. One type is bundles of discrete glass micro-capillaries. Another type consists of one dimensional, integrated arrays of microchannel patterned in bonded glass plate pairs, such as described and claimed in U.S. Pat. No. 5,877,580 issued Mar. 2, 1999. The input sample insertion geometry involves a right angle connection to the microchannel, such as the typical prior art L-load input well for microchannel plates, or a T-load input well, such as described and claimed in copending application Ser. No. 09/178,778 filed Oct. 26, 1998, entitled A T-Load Microchannel Array and Fabrication Method, assigned to the same assignee. These right angle connections to the microchannel results in a three dimensional injection volume of the sample onto the end of the drift gel in the microchannel, which in turn, is a fundamental limit of resolution; the gel-loading buffer fluid interface is defined by convection and diffusion and is difficult to control, partially, because the input hole well overlaps the microchannel end. Also, the loading procedure such as sample size and exact location, insertion method, loading field, field geometrical dispersion, field modification by sample ions, excess sample flush, time delays before starting run, ionic current heating, etc., dramatically influences resolution because drift and diffusion during the loading process can dominate defining the initial injection volume.

The highest resolution has been obtained with electrokinetic (ek) loading directly onto a plane perpendicular to a micro capillary axis at its end; even so, the finite transition of gel to loading buffer and also sample self-diffusion is a limit to resolution; i.e. the loading plane has a finite thickness.

The present invention resolves these prior problems by providing electrodes for the L-load or the T-load for planar, high density, integrated, microchannel arrays. The invention enables higher resolution by concentrating the DNA sample into a narrow strip and holding it there until all the loading is finished and the run starts. Use of an optional second electrode can alleviate the adverse response of impurity ions often present in the DNA sample. An additional electrode may be located in or on the input hole to better define the initial loading.

SUMMARY OF THE INVENTION

It is an object of the present invention to provide an improved input port geometry for planar microchannel arrays.

A further object of the invention is to provide injector-concentrator electrodes for microchannel electrophoresis.

A further object of the invention is to provide an input port geometry which utilizes injector-concentrator electrodes for microchannel arrays that enables efficient extraction and injection of the DNA sample from a single input port.

Another object of the invention is to provide an injector-concentrator electrode for both the L-load or the T-load microchannel electrophoresis configurations.

Another object of the invention is to improve the resolution of L-load or T-load microchannel instruments by electrodes positioned for concentrating the sample into a narrow strip and holding it there until all the loading is finished and the run starts.

Another object of the invention is to utilize an electrode to alleviate the adverse response of impurity ions often present in the example.

Another object of the invention is to provide an electrode in or on the input hole to better define the initial loading.

Another object of the invention is to provide an input port geometry which utilizes multiple electrodes to enable improvement in loading, separation, trapping, and concentration of a planar microchannel instrument.

Other objects and advantages of the present invention will become apparent from the following description and accompanying drawings. Basically, the present invention provides an improved input geometry for planar microchannel arrays which utilizes electrodes to enable improved loading, separation, trapping, and concentration of samples. The electrode arrangement may be utilized with both L-load and T-load microchannel arrays. The invention results in: 1) higher resolution geometry-axially very narrow DNA injection into the channel, 2) more tolerant sample insertion procedure, 3) more tolerant of sample preparation impurities, and 4) efficient 2-D (e.g. Titer format) sample input and injection.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

The present invention is directed to an input port geometry which utilizes injector-concentrator electrodes in planar microchannel arrays that enables efficient extraction and injection of the sample from a single input port. The input port geometry of this invention allows simultaneous concentration, in different channels, of the sample into a longitudinally narrow strip just before releasing it for a run with enhanced injection spatial resolution, and time resolution.

The present invention involves the use of an electrode in the area adjacent the input ports, for the L-load or the T-load for planar, high density, integrated, microchannel arrays. Use of an optional second electrode in spaced relation to the first electrode can alleviate the adverse response of impurity ions often present in a DNA sample. A third electrode in or on the input hole can better define the initial loading.

Figure 1:
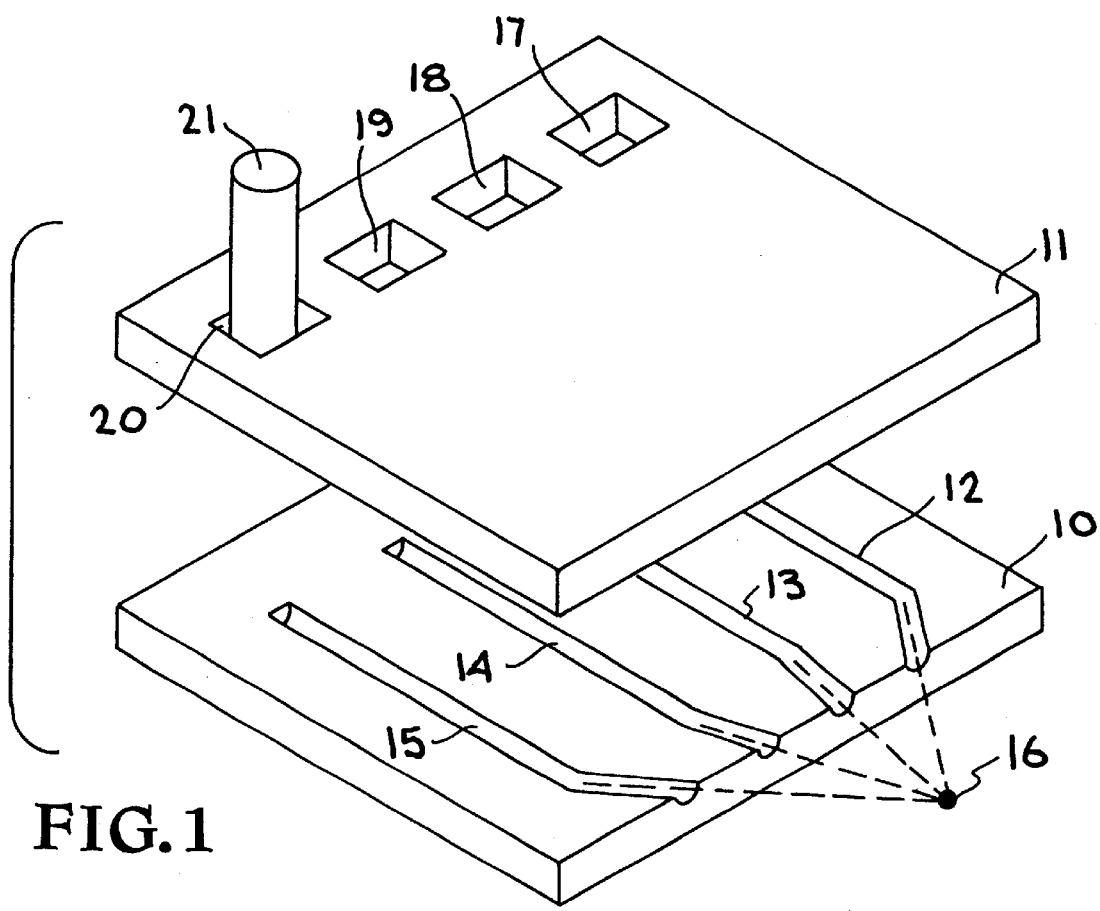
FIG. 1 is an exploded view of a planar microchannel plate assembly.
Figure 2:
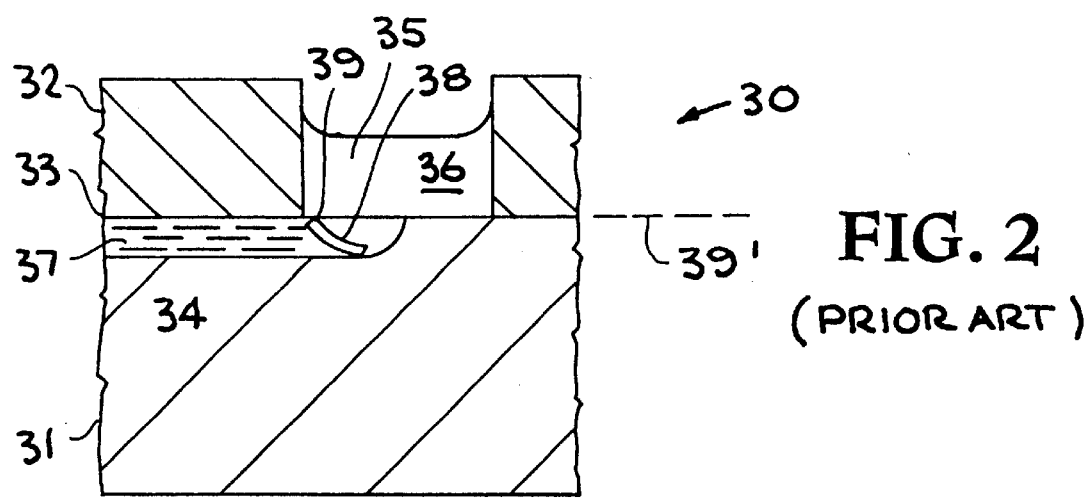
FIG. 2 is a cross-sectional view of a typical prior art L-load input well for microchannel plates, such as that of FIG. 1.
Figure 3:
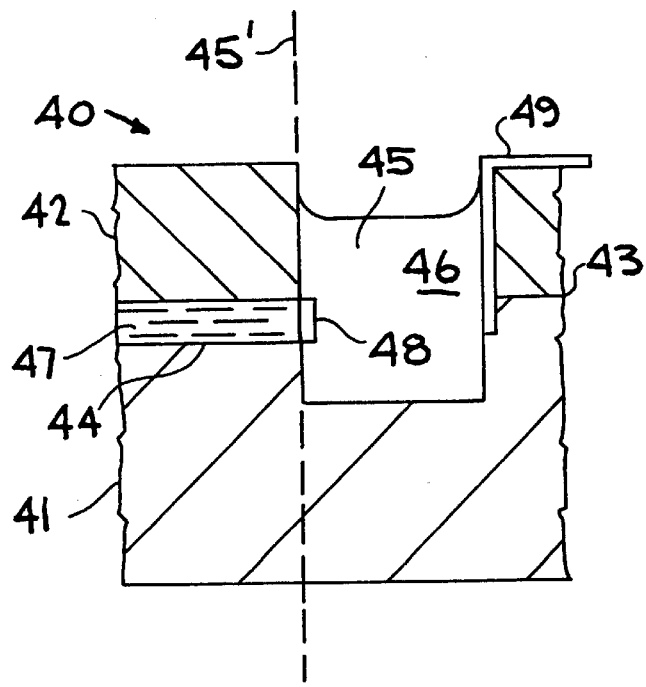
FIG. 3 is a cross-sectional view of an embodiment of a T-load input well for microchannel plates, such as that of FIG. 1.
Figure 4:
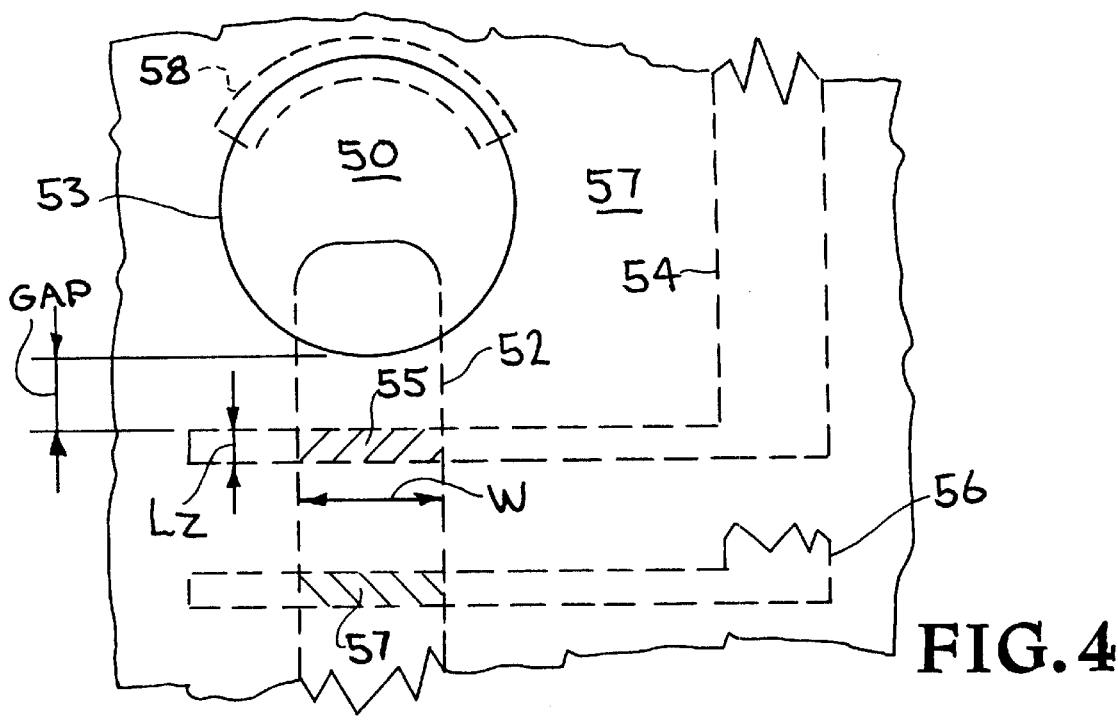
FIG. 4 schematically illustrates a top view of a microchannel plate assembly with an embodiment of an electrode arrangement for a single channel of a microchannel plate assembly, as shown in FIG. 1.

For the best resolution, i.e. chemical separation, it is extremely important to have a very narrow injection zone in the longitudinal or drift axis of a microchannel array; good resolution becomes increasingly difficult if the initial start condition has too long an injection zone, where the peaks are initially all overlapped. Diffusion is always present, but is also more of a problem if the initial injection is too long, either in space or time. FIG. 1 illustrates an embodiment of a microchannel plate or assembly for electrophoresis applications, and FIGS. 2 and 3 illustrate typical L-load and T-load input port geometries, with FIG. 4 illustrating the invention as applied to an L-load type input port. While only one input port is illustrated with the concentrator electrode arrangement of the present invention, it is to be understood that in a multichannel array, such as illustrated in FIG. 1, each input port would be provided with a concentration electrode arrangement illustrated in FIG. 4 and described in detail hereinafter.

The concentrator electrodes are fabricated onto the glass plates, so that they cross the drift channel in a narrow strip at the bond plane. The strip may be as small as 5–15 micrometers, and this strip should be close to the inlet port or hole, but far enough away to accommodate location tolerances (~50–80 micrometers). It should be passivated to be nonconductive at the channel surface and nonreactive to prevent sample electrolysis or degradation or binding. In current loading procedures (without concentrator electrodes), the samples are introduced at about approximately the ends of the microchannels, electrically loaded, excess sample rinsed out, and the run started. A gel to input hole fluid transition region, the divergent field at the microchannel-hole interface, and different settling and loading times that allow diffusions, make it difficult to get the conventional L-load to have a consistent or very short injection zone-perhaps about 100–400 micrometers is typical.

The present invention addresses this loading problem (which also exists in capillaries to some extent) by following the initial volumetric/ek sample load with one or more concentration cycles. If the sample is contaminated with a large number of negative highly mobility impurity ions, such as chlorine (Cl), then a positive concentrator electrode bias will tend to have its attractive field screened fairly quickly by the impurity ions, before the DNA can accumulate. So for impure samples, a second electrode is biased first, so it attracts most of the impurity ions quickly, then the first electrodes, located closer to the hole, is biased enough to attract the less mobile DNA, but not enough to attract the impurity ions that are captured at the second electrode. Thus, just before run time, the DNA is temporarily captured and concentrated on the width of the electrode and much shorter longitudinal length, as seen in FIG. 4, than the above-described prior loading arrangement. Thus, the initial injection condition is very short (5 to 15 micrometers), enabling the best possible resolution from narrow and reproducible injection conditions. Even if the initial sample volumetric/loading and ek deposition is not very reproducible from one channel to the next, this invention will enable extremely reproducible, channel-to-channel and channel-repeated, geometry for the initial injection shape and to a somewhat lessor extent, the sample amount. As seen in FIG. 4, an additional or third electrode located in or on the input hole or port can better define the initial loading.

The attractive features provided by the present invention are the initial loading, impurity ion separation and trapping, and most importantly the final sample concentration in a narrow strip, which are accomplished with multiple local electrodes at the microchannel input region. Multiple electrodes enable the separate features of loading, separation and trapping, and concentration.

Referring now to the drawings, FIG. 1 is an exploded view of a microchannel plate similar to that of about-referenced U.S. Pat. No. 5,877,580 in which the lower or bottom plate or member contains an array of microchannels and the upper or top plate or member contains input wells for the microchannels and control means therefore. The top and bottom plates 10 and 11 may, for example, be composed of glass or plastic. The bottom plate or member 10 contains a plurality of microchannels 12, 13, 14, and 15 which, in this embodiment, are configured to discharge onto a focus point 16. The top plate or member 11 is provided with four square or circular input wells 17, 18, 19, and 20, an optional fill pipe 21 is shown inserted into input well 20. When plates 10 and 11 are bonded together, input wells 17–20 are aligned with the input ends of microchannels 12–15.

The prior art input well geometry for microchannel arrays is of an L-load configuration, as shown in FIG. 2, wherein a cross-section of a microchannel plate generally indicated at 30 is illustrated. The microchannel plate 30 consists of a lower or bottom plate or member 31 and an upper or top plate 32, which are bonded together as indicated at 33 and with bottom plate 31 having an array of microchannels 34 form therein, only one shown, and top plate 32 having a plurality of input wells 35, only one shown, containing a sample or buffer material 36. As known in the art, the microchannels 34 contain a gel or separation drift medium 37, and thus there is a gel-buffer interface volume, as indicated at 38, adjacent the end 39 of microchannel 34. As seen in FIG. 2, the input well 35 overlaps the microchannel 34 and terminates adjacent the upper surface of microchannel, whereby the connection fluid passage from the input well 35 defines a plane perpendicular to the plane of interconnections of plates 31 and 32 and to the plane the microchannel 34, as indicated by the dotted line 39', and to the microchannel 34 involves a right angle; this results in a three-dimensional injection volume of the sample or buffer material onto the end of the drift gel in the microchannel 34, which in turn is a fundamental limit of resolution; the gel-loading buffer fluid interface volume 38 is defined by convection and diffusion and is difficult to control because the input well overlaps the microchannel end 39.

In fabrication of the L-load well of FIG. 2, the microchannels 34 are formed, as by etching or embossing, in the upper surface of bottom plate 31, which may be composed of glass or plastic, the input wells 35 are formed in the upper plate 32, as by drilling, etching or casting, the upper plate 32 being composed of glass or plastic, whereafter the plates 31 and 32 are fusion bonded or otherwise secured together following precise alignment of the input wells with the ends or the microchannels. Thus fabrication of the microchannel plate 30 of FIG. 2 is alignment critical, which increases the cost of manufacture.

FIG. 3 illustrates an embodiment of a T-load input well of above-reference copending application Ser. No. 09/178,778, which involves 3-D geometry input wells, (either "blind" or "thru") for planar, high density, integrated, microchannel arrays. The result of the T-load input well geometry is that the microchannels end abruptly in a plane perpendicular to the microchannel; the right angle channel connection is eliminated. In the prior (FIG. 2) L-load arrangement, the ends of the microchannels overlap the input well; gel flush and loading buffer solution use smears out the gel-buffer fluid interface as determined by both convection and diffusion. The use of T-loads allows the excess gel to more easily be sheared off and rinsed out and establish a fluid interface at the end of the microchannel, albeit still limited by diffusion. The blind T-load (FIG. 3) can be formed by a second shallow machining or etching operation in the bottom plate, which merely extends the length of the input well beyond the end of the microchannel. Alternately, the FIG. 3 blind T-load input wells can be fabricated by drilling the bonded plate pair simply over the ends of the microchannels, which eases the accuracy of the drilling since it only needs to shear off the ends of the microchannels; the drilling itself is much easier and less costly than the precise alignment procedures required for the prior L-load input well.

Referring now to FIG. 3, an embodiment of the "blind" T-load input well is illustrated in cross-section. The term "blind" is from the input well only extending partially into the bottom plate. As shown, a microchannel plate 40 comprises bottom and top plates 41 and 42, bonded together at 43, with bottom plate 41 having microchannels 44, only one shown, and an input well 45 is formed in the top plate 42 and a portion of bottom plate 41 containing a buffer or sample fluid 46. In this "blind" T-load input well arrangement, a gel-buffer interface volume 48 between a gel 47 in the microchannel 44 and the buffer or sample fluid 46 in input well 45 is located along a side wall surface of the input well 45, the end of microchannel 44 being sheared off so as to be perpendicular to the axis of the input well 45, which enables sample or buffer material injection onto a plane perpendicular to—and at the end of—the drift or microchannel 44. As seen in FIG. 3, the input microchannel 44 defines a plane perpendicular to the plane of the input well 45, indicated at 45'. One or more electrodes 49 may be formed or deposited on a wall surface of input well 45 and opposite the end of microchannel 44 to assist in electrokinetic sample injection.

Referring now to FIG. 4, which illustrates in plan view an embodiment of the present invention incorporated into an L-load input well, such as shown in FIG. 2, which illustrates a section of a microchannel plate assembly such as illustrated in FIG. 1, having a bottom plate or member 50 and a top plate or member 51 composed of glass, plastic, etc. and bonded together to form a bond plane therebetween such that a drift channel or microchannel 52 in bottom plate 50 is in alignment with an input port or hole 53 in top plate 51. A first injection-concentrator electrode 54 is formed in either of plates 50 or 51 so that it crosses a width W of the microchannel 52 at the bond plane as a narrow strip 55 width Lz, which may be 5–15 micrometers for example. The strip 55 is located as indicated by a gap G, about 50–80 micrometers from the input port or hole 53 to accommodate location tolerances, and should be passivated to be nonconductive at the surface of the microchannel 52 and nonreactive to prevent sample electrolysis or degradation or binding. The strip 55 functions to concentrate the sample, as discussed above. As second (optional) concentrator electrode 56 is formed in either of the plates similar to electrode 54 and includes a narrow strip 57 having a width Lz, which extends across microchannel 52, and is located a distance of 50 to 500 micrometers from strip 55 of electrode 54. As pointed out above, the optional second electrode 56 functions to separate and trap negative high mobility impurity ions, for example. A third electrode 58 having a width of 5 to 300 micrometers is formed in or on the input port or hole 53 to better define the initial loading.

As pointed out above, electrodes 54 and 56 are of a different electrical bias, with the bias of the first electrode 54 being less than that of second electrode 56. By way of example the bias on electrode 54 may be +1V to +2V, while the bias on electrode 56 may be +1.2V to +2.2V. While not shown the electrodes 54, 56 and 58 would be connected to electrical power supplies having voltages in the range of 0 to +10V. Also, electrode 58 is biased at ground, for example.

It has been shown that the present invention provides an input port geometry, with injector-concentrator electrodes, that enable efficient extraction and injection of DNA sample, for example, from a single input port of a planar microchannel array for electrophoresis. This invention may be effectively utilized in capillary electrophoresis, chemical flow injection analysis, liquid chromatography, enhanced electrokinetic injection, chemical reaction microchannel flow systems, all in bonded glass, plastic, or other insulator microfluidic structures and systems. The invention utilizes electrodes to enable the separate features of initial loading, impurity ion separation and trapping, and most importantly the final sample concentration in a narrow strip.

While particular embodiments of the invention, certain of which may be optional along with parameters, etc. have been described and illustrated to exemplify and teach the principles of the invention such are not intended to be limiting. Modifications and changes may become apparent to those skilled in the art, and it is intended that the scope of the invention be limited only by the scope of the appended claims.

What is claimed is:

1. In a planar microchannel instrument having at least one microchannel and an input port located at one end of the at least one microchannel, the improvement including an electrode located adjacent said microchannel for concentrating a sample passing from the input port into the microchannel,
   said electrode having a strip which extends adjacent the width of the at least one microchannel, and
   an electrode located in or on the input port for improving initial loading of a sample.

2. The improvement of claim 1, additionally including an electrode located adjacent the at least one microchannel and spaced from said first-mentioned electrode for separating and trapping impurity ions in a sample.

3. The improvement of claim 1, wherein said narrow strip of said electrode has a width of about 5–15 micrometers.

4. The improvement of claim 3, wherein said narrow strip of said electrode is located at a distance of about 50 to about 80 micrometers from said inlet port.

5. The improvement of claim 2, wherein said electrode for separating and trapping impurity ions in a sample has a narrow strip which extends adjacent the width of the at least one microchannel, and is located at a distance of about 50 to about 500 micrometers from said electrode for concentrating a sample.

6. The improvement of claim 5, wherein said narrow strip has a width of about 5–15 micrometers.

7. The improvement to claim 1, wherein said electrode for improving loading of a sample extends at least partially around the input port, and has a width of about 5 to 300 micrometers.

8. The improvement of claim 2, wherein each of said electrodes have a different electrical bias applied thereto.

9. The improvement of claim 8, wherein the bias on said electrodes is positive when high mobility impurity ions in a sample are negative, and the positive bias on said second electrode is greater than the positive bias on the first electrode, whereby said second electrode quickly attracts the impurity ions.

10. An input port geometry for planar microchannel arrays for application such as electrophoresis that enables efficient extraction and injection of a DNA sample from a single input port, comprising:
   an electrode located at a distance from said input port for concentrating a sample to be injected into a microchannel, and
   an electrode located in or on said input port for preconcentrating the initial loading of a sample.

11. The input port geometry of claim 10, additionally including a second electrode located at a distance from said first-mentioned electrode for separating and trapping impurities with different mobilities from sample ions in a sample.

12. The input port geometry of claim 11, wherein each of said electrodes includes a strip having a width of about 5 to about 15 micrometers which is located and extends adjacent a width of a microchannel.

13. The input port geometry of claim 12, wherein said distance from said first-mentioned electrode to said second electrode is about 50 to about 500 micrometers.

14. The input port geometry of claims 13, wherein said first-mentioned electrode is about 50 to about 80 micrometers away from the input port.

15. The input port geometry of claim 10, additional including an electrode located in or one said input port for better defining the initial loading of a sample.

* * * * *